(12) United States Patent
Yanagi

(10) Patent No.: US 6,520,906 B2
(45) Date of Patent: Feb. 18, 2003

(54) COITUS ASSISTANCE DEVICE FOR MALES

(76) Inventor: Senji Yanagi, 7-10-303, Nakaochiai 2-chome, Shinjuku-ku, Tokyo (JP)

( * ) Notice: Subject to any disclaimer, the term of this patent is extended or adjusted under 35 U.S.C. 154(b) by 0 days.

(21) Appl. No.: 09/900,911

(22) Filed: Jul. 9, 2001

(65) Prior Publication Data

US 2003/0009082 A1 Jan. 9, 2003

(51) Int. Cl.⁷ .................................................. A61F 5/00
(52) U.S. Cl. ........................ 600/38; 128/842; 128/918
(58) Field of Search ................................ 128/842, 844, 128/918; 604/347–353; 600/38–41

(56) References Cited

U.S. PATENT DOCUMENTS

| | | | | |
|---|---|---|---|---|
| 4,495,254 A | * | 1/1985 | Hoffman | 428/632 |
| 5,192,271 A | * | 3/1993 | Kalb | 600/38 |
| 5,599,275 A | * | 2/1997 | France | 600/38 |
| 5,810,710 A | * | 9/1998 | Burgos | 600/38 |

FOREIGN PATENT DOCUMENTS

| | | |
|---|---|---|
| JP | 60 108211 | 7/1965 |
| JP | 1126220 | 8/1989 |
| JP | 5 39525 | 5/1993 |

* cited by examiner

Primary Examiner—Michael A. Brown
(74) Attorney, Agent, or Firm—Jordan and Hamburg LLP

(57) ABSTRACT

A gold band having a length normally required and a width as normally required is flexible such that the gold band can be freely bent inward to form an oval ring of dimensions as normally required to oppress the root part of the inserted penis enlarged by erection. The gold band includes overlapping portions at opposed ends thereof which are overlapped to form the oval ring. Patterned protrusions for oppressing the urogenital canal in the root part of the erect penis enlarged by erection are provided over a specified area at the entry of the inner surface of the gold band.

15 Claims, 4 Drawing Sheets

(A)

(B)

(A)

(B)

COITUS ASSISTANCE DEVICE FOR MALES

BACKGROUND OF THE INVENTION

This invention relates to a coitus assistance device for males which can be effectively used for maintaining the penis in the erect state for a long time during sexual intercourse or giving assistance to those males who suffer from impotence or premature ejaculation in particular.

For married couples, coitus dysfunction of men, erectile dysfunction in particular, is quite likely to become a serious problem in their married life. In medical terms, erection of the penis requires about six times the blood flow as that in the non-erect state with an increase in the amount of cyclic GMP, which is an erection-causing substance, in the vasoganglion (blood vessel network) in the corpus cavernosum by the action of nitrogen monoxide which increases the blood flow. Immediately after ejaculation, cyclic GMP is dissolved by a substance called phosphodiesterase, which shrinks the penis. Patients with erectile dysfunction are unable to maintain the penis in the erect state because cyclic GMP in them does not increase sufficiently due to certain causes.

As a specific medicine for cases of coitus dysfunction, a new drug called "Viagra" has been successfully introduced into the market to the delight of many male patients. Viagra blocks the action of phosphodiesterase and consequently retards the dissolution of cyclic GMP so as to assist erectile function. According to clinical research conducted within the country (U.S.A.), 70% of the subjects experienced the positive effect of the drug.

However, the Viagra drug produces side effects and many such cases have been reported. For example, a person suffering from heart disease or high blood pressure or whose heart is enfeebled from physical fatigue who takes Viagra and has sexual intercourse, increases the burden on his heart to such an extreme extent that he may die from shock during intercourse in bed. Base d on this finding, persons who have developed neurological disorders or peripheral circulation deficiencies from diabetes mellitus, a narrowing of vessels in the lower limbs due to arteriosclerosis, other organic diseases, or those who have developed heart diseases should not use this drug. Furthermore, the drug should not be taken together with a hypotensor or an anti-angina drug. It is dangerous to take this drug carelessly without taking into consideration the physical condition, merely in expectation of erectile effect. The drug is also rather expensive.

SUMMARY OF THE INVENTION

Major objects of the present invention to solve the above-mentioned problems are as follows.

A first object of the present invention is to provide a coitus assistance device which is most suitable for males who suffer from coitus dysfunction such as impotence or premature ejaculation.

A second object of the present invention is to provide a coitus assistance device which can be used without the need for previous medical examination before use regardless of the user's physical condition, and without fear of side effects.

A third object of the present invention is to provide a coitus assistance device which can be used repeatedly over an indefinite period for maximum cost performance and minimum price.

Other objects of the present invention will become apparent from the descriptions included herein in the specification, drawings, and claims in particular.

For the purpose of solving the above-mentioned problems, the present invention employs a constituent structure characteristic to the present invention, wherein a gold band having a length as normally required and a width as normally required is flexible to be freely bent inward to form a roughly oval-shaped ring of dimensions as normally required to oppress the root part of the inserted penis enlarged by erection, overlapping portions are prepared at the two ends of said gold band to be overlapped to form said ring, and patterned protrusions for oppressing the urogenital canal in the root part of the erected penis enlarged by erection are provided over a specified area at the entry of the inner surface of said gold band.

More specific descriptions of the characteristics and novel features in conjunction with the structure employed in the present invention for the purpose of solving the above-mentioned problems are presented below.

A first feature of the present invention provides a coitus assistance device for males comprising a gold band having a length as normally required and a width as normally required, said gold band being flexible to be freely bent inward to form a roughly oval-shaped ring of dimensions as normally required, overlapping portions prepared at the two ends of said gold band to be overlapped to form said ring, and patterned protrusions for oppressing purpose over a specified area at the entry of the inner surface of said gold band.

A second feature of the present invention provides a coitus assistance device for males according to the first feature above, wherein said dimensions as normally required of said ring are sufficient to oppress the root part of the penis enlarged by erection.

A third feature of the present invention provides a coitus assistance device for males according to the first or second feature above, wherein said length as normally required of said gold band is of the order of 10 to 12 cm.

A fourth feature of the present invention provides a coitus assistance device for males according to the first, second, or third feature above, wherein said width as normally required of said gold band is a maximum of 0.8 to 1.0 cm at the center portion of said gold band.

A fifth feature of the present invention provides a coitus assistance device for males according to the first, second, third, or fourth feature above, wherein said gold band is made from 24 K gold material, said gold band gradually narrowing in width moving away from said center portion towards its two ends, said two ends having overlapping portions that are thinner than other portions of said gold band.

A sixth feature of the present invention provides a coitus assistance device for males according to the first, second, third, fourth, or fifth feature, wherein said patterned protrusions for oppressing purpose have a recess formed at the center portion for retaining perfume.

A seventh feature of the present invention provides a coitus assistance device for males according to the fifth or sixth feature, wherein said gold band has a series of edged protrusions formed on the inner surface of said gold band along its longitudinal edges except for the overlapping portions at the two ends of said gold band.

An eighth feature of the present invention provides a coitus assistance device for males according to the fifth, sixth, or seventh feature, wherein said center portion of said gold band becomes roughly linear in form when said gold band is bent to form a roughly oval-shaped ring.

A ninth feature of the present invention provides a coitus assistance device for males according to the fifth, sixth, or seventh feature, wherein said gold band is decorated with die-punched patterns or gold-chased patterns in the portions of said gold band except for said recess formed at the center portion for retaining perfume and said overlapping portions prepared at the two ends of said gold band, said gold band being capable of serving as a ring worn on the finger.

BRIEF DESCRIPTION OF THE DRAWINGS

While the specification concludes with claims particularly pointing out and distinctly claiming the subject matters of the present invention, it is believed that this invention will be better understood from the following description taken in connection with the accompanying drawings in which:

DETAILED DESCRIPTION OF THE INVENTION

Embodiments of the present invention are described herein with reference to the accompanying drawings.
<Embodiment 1>

Figure 1:
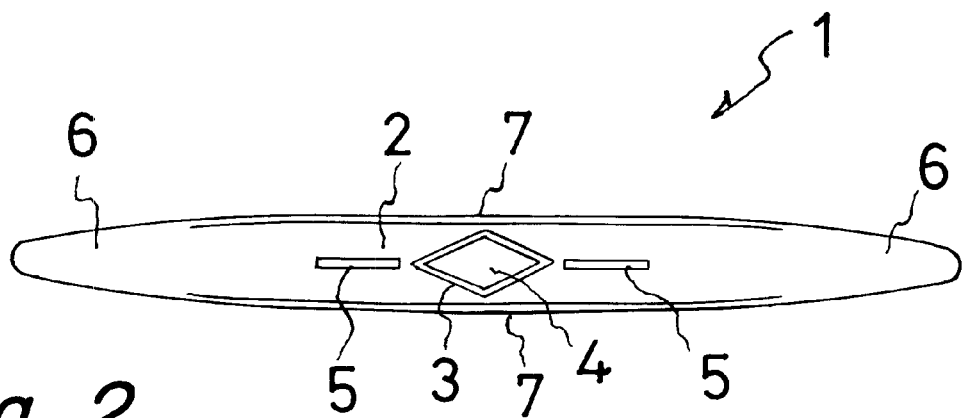
FIG. 1 shows the plan view of the inner side of the gold band according to the present invention in an embodiment.
Figure 2:
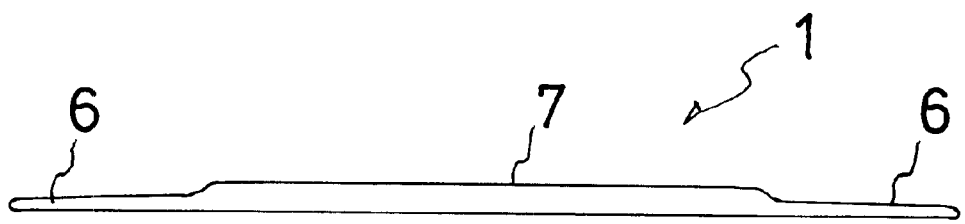
FIG. 2 shows the front view of the gold band according to the present invention in the same embodiment as FIG. 1.
Figure 3:
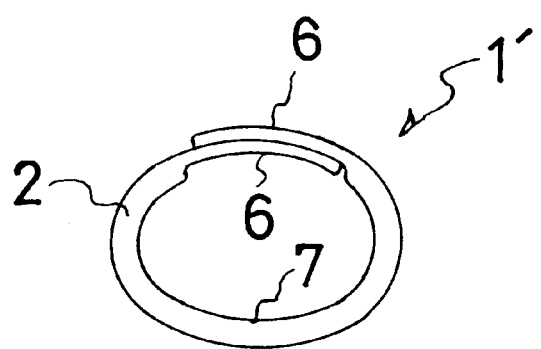
FIG. 3 shows the end view of the gold band according to the present invention bent to form an oval-shape ring.
Figure 4:
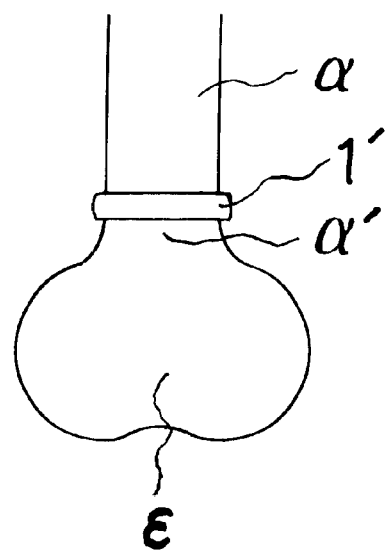
FIGS. 4 (A) and (3) show the oval ring worn with the penis erected and the same with the penis not erected respectively.
Figure 4:
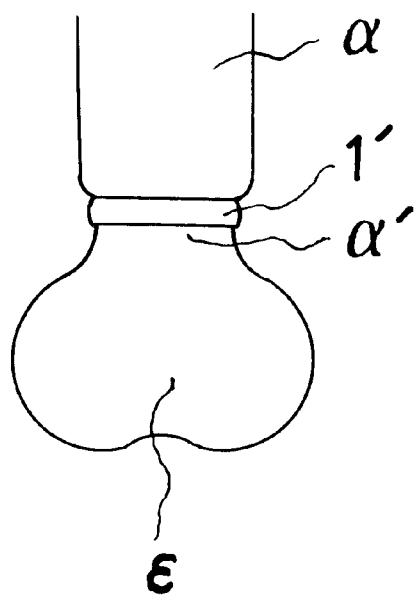
Figure 5:
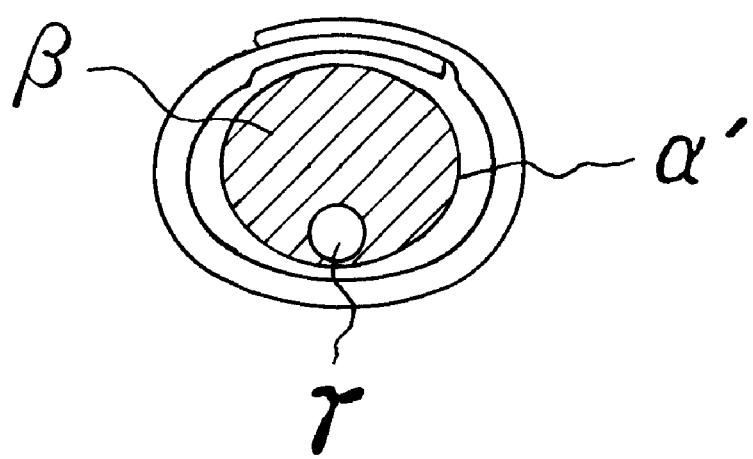
FIGS. 5 (A) and (B) show cross-sectional views of the root part of the penis with the oval ring worn with the penis erected and not erected respectively, associated with FIGS. 4 (A) and (B) above.
Figure 5:
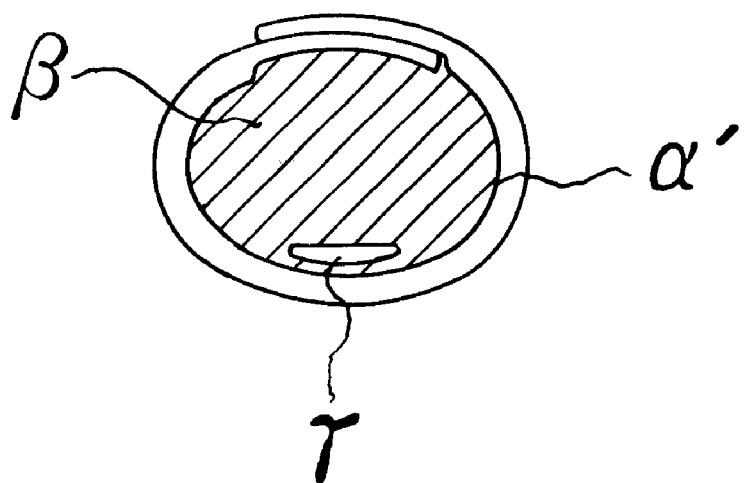

FIG. 1 shows the plan view of this embodiment, FIG. 2 shows the front view of this embodiment, FIG. 3 shows the end view of the present invention bent to form a roughly oval-shape ring, FIGS. 4 (A) and (B) show the oval ring worn with the penis erected and the same with the penis not erected, and FIGS. 5 (A) and (B) show cross-sectional views of the root part of the penis with the oval ring worn with the penis erected and not erected.

FIG. 1 shows the following parts. "1" shows an embodiment of the present invention, a coitus assistance device for males. "2" is a 24 K gold band which can be freely bent. "3" indicates a diamond-shaped patterned protrusion for oppressing purpose with a recess 4 inside for retaining perfume. "5" indicates a pair of bar-shaped protrusions on both sides of said diamond-shaped protrusion as part of the patterned protrusions for oppressing purpose. "6" shows overlapping portions prepared at the two ends of said gold band. "7" indicates edged protrusions formed on the inner surface of said gold band along its longitudinal edges except for the overlapping portions.

In this embodiment of the invention with the above-mentioned practical specifications, preferably the gold band "2" is prepared in good time before sexual intercourse. With the patterned protrusions for oppressing purpose "3" facing the inner side of the ring, the gold band should be bent to form an oval ring "1" a little larger than the dimension of the root part α' of the penis in the non-erect state α such that the ring is wound around the root part of the second joint in the thumb and the two overlapping portions at the two ends of said gold band are overlapped in place. As the center portion of said gold band is mechanically stronger than other portions of said gold band due to the presence of the patterned protrusions and the largest width of said gold band, preferably said center portion should become roughly linear in form. Once said oval ring "1" is formed, the bending process need not be repeated when using said gold band next time.

Then, said recess 4 for retaining perfume should be directed upward so that a drop of perfume may be placed on it. While handling said gold band carefully so as not to spill the perfume out of the recess, push the ring thus formed as mentioned above over the penis to the root part α' of the penis α in the non-erect state (for example, at a point 1 cm from the root part of the penis). With direct and indirect visual or tactual stimulation applied to erect the penis, including such techniques as looking at pornography or masturbating the penis α, blood flow should be increased and the corpus cavernosum β should be enlarged and cause an erection. The symbol ε in FIG. 4 indicates the scrotum.

While in the state established by the preparation described above, the oval ring 1' oppresses the root part α' of the penis α to block the back-flow of blood and cyclic GMP and also to block the influx of the enzyme phosphodiesterase after ejaculation so that the erected state of the penis will last longer. One of the likely consequences includes an increase in the amount of sperm. As for ejaculation, with the urogenital canal γ oppressed strongly with the patterned protrusions 3 for oppressing purpose and edged protrusions 7, the amount of ejaculated sperm will be reduced to about one third of that in ordinary ejaculation. This reduction of ejaculated sperm means a decrease in the amount of energy required for sexual intercourse. This effect of the present invention indicates that the invention is suitable for those who have little physical strength, such as late-middle-aged persons or older, persons who are not confident in their own physical strength, and those who suffer from impotence, premature ejaculation, or heart diseases.

In conjunction with the use of a condom which is generally considered to be effective in preventing the transmission of sexually transmitted diseases including AIDS, placing the oval ring 1' on the root part α' of the penis α over the condom worn over the penis will hold the condom firmly and prevent the condom from slipping off accidentally or the leakage of sperm. In other words, the present invention secures the function of a condom as a barrier against germs and as a contraceptive means.

The perfume retained in said recess 4 for retaining perfume will have a mood-enhancing effect. With pure gold used for said gold band, no rust or harmful substance will be produced that could cause trouble or damage to the human body. On the contrary, gold will be beneficial for the user.
<Embodiment 2>

Figure 6:
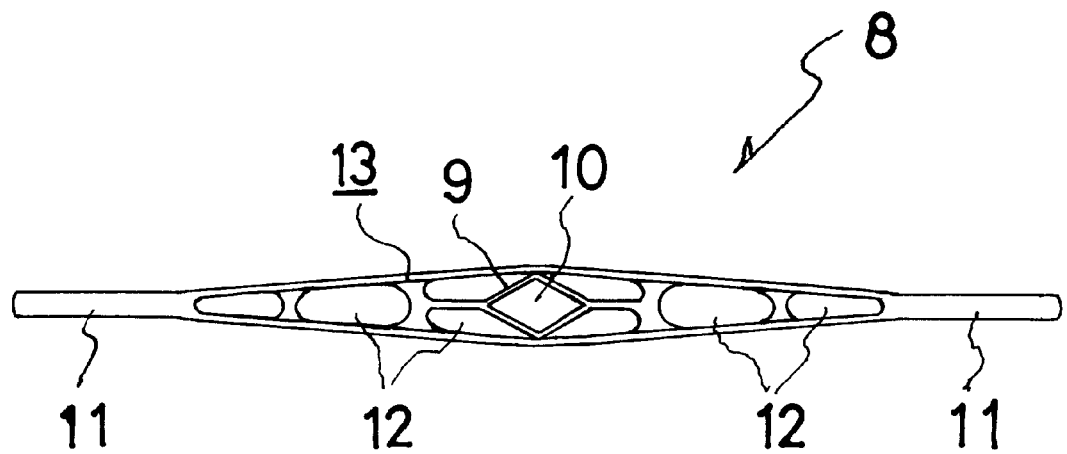
FIG. 6 shows the plan view of the inner side of the gold band according to the present invention in another embodiment.
Figure 7:
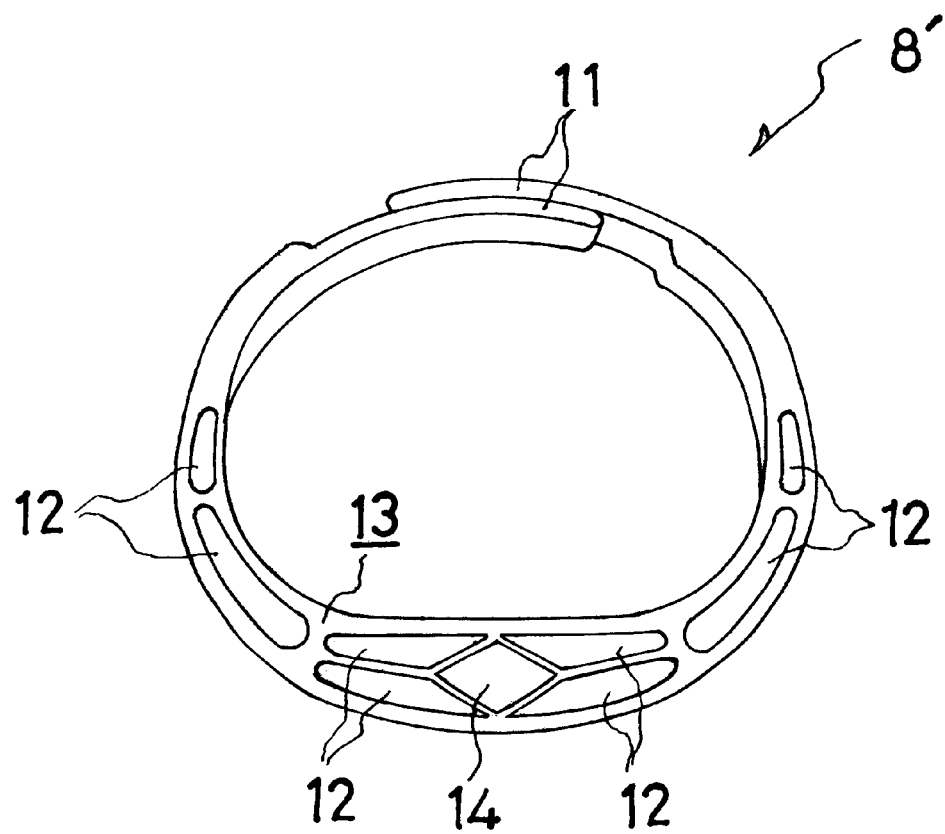
FIG. 7 shows the enlarged oblique front view of the oval ring formed by bending said gold band shown in FIG. 6 above.

FIG. 6 shows a plan view of the inner side of the gold band according to the present invention used in another embodiment. FIG. 7 shows the enlarged oblique front view of an oval ring formed by bending said gold band.

The coitus assistance device 8 for males in Embodiment 2 is different from the coitus assistance device 1 for males in Embodiment 1 in that said gold band 13 is decorated with die-punched patterns or gold-chased patterns 12 in the portions of said gold band except for said recess 10 for retaining perfume at the center portion formed with the patterned protrusion 9 for the oppressing purpose and said overlapping portions 11 prepared at the two ends of said gold band, and thus upgraded gold band 13 should be bent to form a circular ring whose diameter is smaller than that of the oval ring shown in FIG. 8 to be used as a finger ring when it is not used for the purpose described in Embodiment 1. The drawing of said circular ring is not presented herein. The user may attach a jewel 14 such as a hemispherical cat's-eye, agate, opal, or flat pearl in the center position outside of the band for enhanced value as a ring.

Other aspects of the present invention in Embodiment 2 are the same as in the coitus assistance device 8 for males in Embodiment 1. When it is used as the coitus assistance device 8 for males, the ring can be enlarged to form an oval ring having the same dimensions as the oval ring 1' in Embodiment 1 as shown in FIG. 7, resulting in the same effect and performance as those in Embodiment 1.

This embodiment allows the user to avoid losing the present invention when not used as a coitus assistance device 8 for males by providing a convenient method to carry the invention and also adds extra value to the invention.

<Working Example>

A working example of the present invention is explained with reference to FIGS. 1 to 3, 6 and 7.

The gold bands 2 and 13 have a length of about 10 to 12 cm, a central width of about 0.8 to 1.0 cm, an end-portion width of about 3 to 5 mm, a central thickness of about 1 mm, and a height of protrusions 3 and 9 of about 0.6 mm.

Pure gold (24K) is used for the gold bands 2 and 13 because of the following reasons.

The male sex organ being an soft organ, it has long been a taboo to use metals for coitus assistance devices 1 and 8 for males. However, pure gold is a suitable material for the purpose of giving elastic resistance to the outer surface of the soft organ penis α since it has the most adequate softness and elasticity of all the metals. In the present invention, oval rings 1' and 8' having an oval-like trapezoidal shape with the size as normally required is formed by bending the gold bands 2 and 13 made from pure gold to the size of the root part α' of the penis α.

The oval rings 1' and 8' is used in a trapezoidal shape in an embodiment in order to secure the blood flow paths on both sides of the corpus cavernosum β when the penis is erected for increasing blood circulation within the body, which maintains the penis in the erected state for a long time. In this sense, a conventional ring-shaped coitus assistance device (whose drawing is not presented herein) oppresses the outer surface of the root part α' of the penis α evenly, thus blocking the blood circulation inside the corpus cavernosum β and having a contrary effect, which makes it difficult to maintain the penis in the erected state for a long time.

The shorter diameter in the vertical direction and the longer diameter in the horizontal direction of the oval rings 1' and 8' should be in the proportion of 2:3 approximately. For example, the oval ring should have a short diameter of 2.0 cm and a long diameter of 3.0 cm (on average).

Needless to say, since penis size differs from one person to another, the size of the oval rings 1' and 8' mentioned above is given as a representative example or guideline value. According to a survey conducted by the applicant of the present invention, individual differences are in the range of 5 mm only. For example, a person on the smaller side may have a root part α' of the penis α measuring 1.8×2.5 cm, while another person on the larger side may have a root part measuring 2.5×3.5 cm. As a result, adjustment of the oval rings 1' and 8' within a maximum of 1.0 cm range is sufficient to cover different individuals.

The reason why the adjustment of the oval rings 1' and 8' requires a 1-cm range while the individual differences of the root part α' of the penis α remain in the 5-mm range is that the corpus cavernosum β expands in the right/left directions as the root part α' of the penis α is oppressed upward and downward.

Assuming that the size of the oval rings 1' and 8' is fixed for the average dimensions mentioned above, for example following the 2×3-cm standard, the individual differences may be offset by the soft nature of the penis α. However, the present invention employs pure gold, which has the most adequate softness and elasticity of all the metals, for the gold bands 2 and 13 for complete performance of the coitus assistance device for males and for easy adjustment of the size by each user. The respective dimensions of the coitus assistance device for males, such as thickness and width, mentioned above of the oval rings 1 and 8 are most appropriate values for achieving the adjustable free-size type oval rings 1' and 8' (coitus assistance devices 1 and 8 for males). These values were experimentally obtained by the applicant of the present invention.

The applicant of the present invention conducted experiments and found that the penis α of a late-middle-aged person who suffered from a medium degree of impotence, remained erect for two hours and 15 minutes with the coitus assistance device 8 for males worn on the penis (the erected state continued further but the experiment was terminated after the time mentioned above had elapsed).

Generally speaking, late-middle-aged persons first become mentally excited, then the penis α becomes erect and ejaculation occurs rather quickly. Based on the results of the experiments on the present invention, it was clear that the coitus assistance devices 1 and 8 for males can maintain the penis α in the erected state regardless of the mental state and can control ejaculation. Furthermore, the subjects of the experiments did not become exhausted by having their penis α erected for a long time. So it can also be concluded that the present invention will have a positive effect regarding various physical functions and will have favorable influences upon the physical and mental states of the user.

The patterned protrusions 3 and 9 for oppressing purpose in the coitus assistance devices 1 and 8 for males can take any shape other than a diamond, such as a circle, triangle, square, polygon, coat of arms, so long as it forms recesses 4 and 10 for retaining perfume.

Though typical preferred embodiments and a working example are described above, the effects and advantages of the present invention are not limited to them. It should be construed that the present invention may be practiced in different manners by changing the application methods within the range of the effects described later in order to fulfill the purposes mentioned above.

With pure gold used for the present invention, said gold band can be bent freely, is easy on the human skin, and does not produce rust. The gold band can be used also as a finger ring. The high-grade finish will also help users to overcome an inferiority complex when using the present invention. The gold band is not harmful at all and its size can be adjusted since it can be freely bent into an oval ring with dimensions matching the size of the root part of the penis of each user.

The present invention, compared with the drug Viagra, does not require prior medical consultation before use. In addition, it does not have to be purchased at high cost after each time of use. It does not cause fear among users of side effects or excessive medical effect by overdose, either. Furthermore, once it is formed into an oval ring, it can be used permanently. It does not burden the heart or other organs. It can be used while maintaining the natural physical state of the user without causing any side effect. With the present invention, the penis erected and enlarged as a result of visual or tactual stimulation can remain hard for a long period that cannot be attained otherwise such as by medication.

In addition to the above, the gold band according to the present invention can be carried easily or worn as a finger ring. It does not require water unlike drugs. It can be used conveniently no matter where the user might be. The user can have sexual intercourse with the oval ring worn on the penis. With the oval ring worn over a condom, the oval ring acts in the same manner as a sock holding device and thus prevents the condom from slipping off accidentally or leakage of sperm, thus preventing unexpected or undesired circumstances by securing the function of a condom as a barrier against AIDS or other sexually transmitted diseases and as a contraceptive means. By adjusting back and forth the position of the oval ring worn on the root part of the penis, the size of the erected penis can be adjusted to suit the female sex organ. The amount of ejaculated sperm will be reduced to about one third of that in ordinary ejaculation. This reduction of ejaculated sperm means a decrease in the amount of energy required for sexual intercourse, which is associated with the resulting state of fatigue. This particular effect of the present invention is suitable for those who have little physical strength or stamina. The user may develop confidence in his sexual potency as he will experience smooth intercourse. The present invention will surely help married couples to continue satisfactory married life.

What is claimed is:

1. A coitus assistance device for males comprising:
    a gold band having a length as normally required and a width as normally required, said gold band being flexible to be freely bent inward to form a roughly oval-shaped ring of dimensions as normally required, overlapping portions prepared at two ends of said gold band and to be overlapped to form said ring; and
    patterned protrusions for oppressing purpose over a specified area at the entry of an inner surface of said gold band, said gold band being made from 24 K gold material, said gold band gradually narrowing in width moving away from a center portion thereof towards the two ends, said two ends having overlapping portions that are thinner than other portions of said gold band.

2. A coitus assistance device for males according to claim 1, wherein said width as normally required of said gold band is a maximum of 0.8 to 1.0 cm at a center portion of said gold band.

3. A coitus assistance device for males according to claim 1, wherein said gold band includes a series of edged protrusions formed on the inner surface of said gold band along longitudinal edges thereof except in the overlapping portions at the two ends of said gold band.

4. A coitus assistance device for males according to claim 1, wherein said center portion of said gold band becomes roughly linear in form when said gold band is bent to form the roughly oval-shaped ring.

5. A coitus assistance device for males comprising:
    a gold band having a length as normally required and a width as normally required, said gold band being flexible to be freely bent inward to form a roughly oval-shaped ring of dimensions as normally required, overlapping portions prepared at two ends of said gold band and to be overlapped to form said ring; and
    patterned protrusions for oppressing purpose over a specified area at the entry of an inner surface of said gold band, said patterned protrusions for oppressing purpose having a recess formed at a center portion for retaining perfume.

6. A coitus assistance device for males according to claim 5, wherein said gold band is decorated with at least one of die-punched patterns and gold-chased patterns in portions of said gold band excluding said recess formed at the center portion for retaining perfume and said overlapping portions prepared at the two ends of said gold band, said gold band being capable of serving as a ring worn on the finger.

7. A coitus assistance device for males comprising:
    a gold band having a length and a width each as normally required, said gold band being freely bendable inward to form a roughly oval-shaped ring such that dimensions thereof become sufficient to oppress both upper and lower sides of a root part of a penis enlarged by erection to a greater extent than both right and left sides thereof, a main portion of said gold band becoming a roughly linear-shaped portion at a bottom of said oval-shaped ring when in use after said gold band is bent, said linear-shaped portion raising an oppressive pressure to be given to the lower side of the root part of the penis to a greater extent than the upper side thereof;
    two overlapping portions respectively prepared at two ends of said gold band, said overlapping portions being overlapped at a top of said oval-shaped ring when in use; and
    a plurality of patterned protrusions protuberantly formed at said main portion of said gold band such that said patterned protrusions are arranged on an inner surface of said linear-shaped portion of said oval-shaped ring when in use, said patterned protrusions thereby further raising the oppressive pressure by said linear-shaped portion.

8. A coitus assistance device for males according to claim 7, wherein said gold band is formed of substantially 24 carat gold.

9. A coitus assistance device for males according to claim 7 or 8, wherein a proportion of a shorter diameter in a vertical direction to a longer diameter in a horizontal direction of said oval-shaped ring is approximately 2 to 3.

10. A coitus assistance device for males according to claim 7 or 8, wherein said gold band gradually becomes narrower in width ranging from a center portion to said two ends thereof.

11. A coitus assistance device for males according to claim 7 or 8, wherein a thickness of said overlapping portions is thinner than any other portions of said gold band.

12. A coitus assistance device for males according to claim 7 or 8, wherein said patterned protrusions include a series of edged protrusions formed at both longitudinal edges of said gold band such that said edged protrusions are arranged on said inner surface of said linear-shaped portion of said oval-shaped ring while in use, said edged protrusions thereby further raising the oppressive pressure by said linear-shaped portion.

13. A coitus assistance device for males according to claim 7 or 8, wherein one of said patterned protrusions formed at a center portion of said gold band such that said one of said patterned protrusions is arranged on said inner surface of said linear-shaped portion of said oval-shaped ring while in use has a recess for retaining perfume therein.

14. A coitus assistance device for males according to claim 13, wherein said gold band is decorated with die-punched patterns in portions of said gold band excluding said recess and said overlapping portions, said gold band being capable of serving as a finger ring.

15. A coitus assistance device for males according to claim 13, wherein said gold band is decorated with gold-chased patterns in portions of said gold band excluding said recess and said overlapping portions, said gold band being capable of serving as a finger ring.

* * * * *